(12) United States Patent
Shah et al.

(10) Patent No.: US 7,595,340 B2
(45) Date of Patent: Sep. 29, 2009

(54) SEROTONIN AND NOREPINEPHRINE REUPTAKE INHIBITOR AND USES THEREOF

(75) Inventors: Syed M. Shah, East Hanover, NJ (US); Mahdi B. Fawzi, Morristown, NJ (US); Eric C. Ehrnsperger, Chestnut Ridge, NY (US); Panolil Raveendranath, Monroe, NY (US)

(73) Assignee: Wyeth, Madison, NJ (US)

( * ) Notice: Subject to any disclaimer, the term of this patent is extended or adjusted under 35 U.S.C. 154(b) by 686 days.

(21) Appl. No.: 11/486,336

(22) Filed: Jul. 13, 2006

(65) Prior Publication Data
US 2007/0015824 A1 Jan. 18, 2007

Related U.S. Application Data

(60) Provisional application No. 60/699,883, filed on Jul. 15, 2005.

(51) Int. Cl.
*A61K 31/35* (2006.01)
*C07D 309/10* (2006.01)

(52) U.S. Cl. .................................. 514/459; 549/419

(58) Field of Classification Search ............... 549/419; 514/459
See application file for complete search history.

(56) References Cited

U.S. PATENT DOCUMENTS

| 4,535,186 A | 8/1985 | Husbands et al. |
| 6,673,838 B2 | 1/2004 | Hadfield et al. |
| 2005/0175698 A1 | 8/2005 | Diorio et al. |
| 2006/0223791 A1 | 10/2006 | Shah et al. |

FOREIGN PATENT DOCUMENTS

| WO | WO 00/32555 A1 | 6/2000 |
| WO | WO 02/064543 A2 | 8/2002 |
| WO | WO 2005/077340 A1 | 8/2005 |
| WO | WO 2006/104791 A1 | 10/2006 |

OTHER PUBLICATIONS

Hall et al, Acute Effects of Atypical Antidepressants on Various Receptors in the Rat Brain, Acta Pharmacol et Toxicol, 54, pp. 379-384, (May 1984).
Klamerus et al, Introduction of a Composite Parameter to the Pharmacokinetics of Venlafaxine and its Active O-Desmethyl Metabolite, J. Clin. Pharmacol 32:716-724 (Aug. 1992).
Testa, Prodrugs Revisted: The "Ad Hoc" approach as a Complement to Ligand Design, Medicinal Research Reviews, vol. 16, No. 3, pp. 233-241, (May 1996).

*Primary Examiner*—Bernard Dentz
(74) *Attorney, Agent, or Firm*—Doina G. Ene; David R. Kurlandsky; A. David Jordan

(57) ABSTRACT

Selective dual serotonin and norepinephrine reuptake inhibitors are provided. These compounds have a lower side-effect profile and are useful in compositions and products for use in treatment of a variety of conditions including depression, fibromyalgia, anxiety, panic disorder, agoraphobia, post traumatic stress disorder, premenstrual dysphoric disorder, attention deficit disorder, obsessive compulsive disorder, social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, borderline personality disorder, fibromyalgia syndrome, diabetic neuropathic pain, chronic fatigue syndrome, pain, Shy Drager syndrome, Raynaud's syndrome, Parkinson's Disease, and epilepsy.

14 Claims, 4 Drawing Sheets

SEROTONIN AND NOREPINEPHRINE REUPTAKE INHIBITOR AND USES THEREOF

CROSS-REFERENCE TO RELATED APPLICATION

This application claims the benefit under 35 USC 119(e) of U.S. Provisional Patent Application No. 60/699,883, filed Jul. 15, 2005.

BACKGROUND OF THE INVENTION

The market for neuroscience and women's health drugs has been moving towards the use of dual serotonin and norepinephrine reuptake inhibitors (SNRI) for first line treatment of various indications, as evidenced by the recent development of SNRI's such as Venlafaxine and Duloxetine. This contrasts with the traditional use of selective serotonin reuptake inhibitors (SSRI). Although the side-effect profile of SSRI's and SNRI's are less severe as compared to older, tricyclic antidepressants compounds, there are still some undesirable side effects related to the selectivity or other neuronal receptor binding (muscarinic, histamine and alpha-adrenergic, etc.) of these SSRI's and SNRI's. Binding to these receptors can lead to side effects such as, dry mouth, drowsiness, appetite stimulation and some cardiovascular risks.

The higher norepinephrine (NE) activity of SNRI's has also been implicated in a number of side effects and therefore limits their application. For example, the currently available SNRI's have limited application for the treatment of irritable bowel syndrome (IBS) because of the constipation side effect associated with higher NE activity. Another potential side effect of SNRI's is that at higher dosages there is a modest increase in diastolic blood pressure and this side effect is associated with higher NE activity. Further, potential overdose situations have been associated with excess adrenergic stimulation, seizures, arrhythmias, bradycardia, hypertension, hypotension and death.

What are needed are alternative compositions for treating conditions associated with serotonin and norepinephrine imbalances, by allowing serotonin and or norepinephrine reuptake inhibition for efficacy with lower post synaptic receptor binding for reduced side-effects [(H. Hall, et al., *Acta pharmacol et. toxicol.* 1984, 54, 379-384)].

SUMMARY OF THE INVENTION

The present invention provides a compound with dual serotonin and norepinephrine reuptake inhibitor activity with low levels of undesirable side-effects.

In one aspect, the invention provides a compound of the structure:

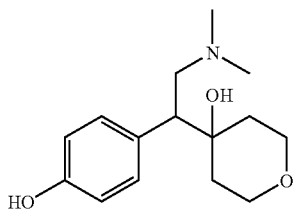

or a prodrug or a pharmaceutically acceptable salt thereof.

In another aspect, the invention provides a pharmaceutical composition comprising a compound of the invention and pharmaceutically acceptable carrier.

In still another aspect, the invention provides a method of using the compound of the invention for treating irritable bowel syndrome, premature ejaculation and urinary incontinence in a subject in need thereof.

In another aspect, the invention provides a pharmaceutical composition comprising a compound of the invention and pharmaceutically acceptable carrier.

Still other aspects and advantages of the invention will be apparent from the following detailed description.

DETAILED DESCRIPTION OF THE INVENTION

Figure 1:
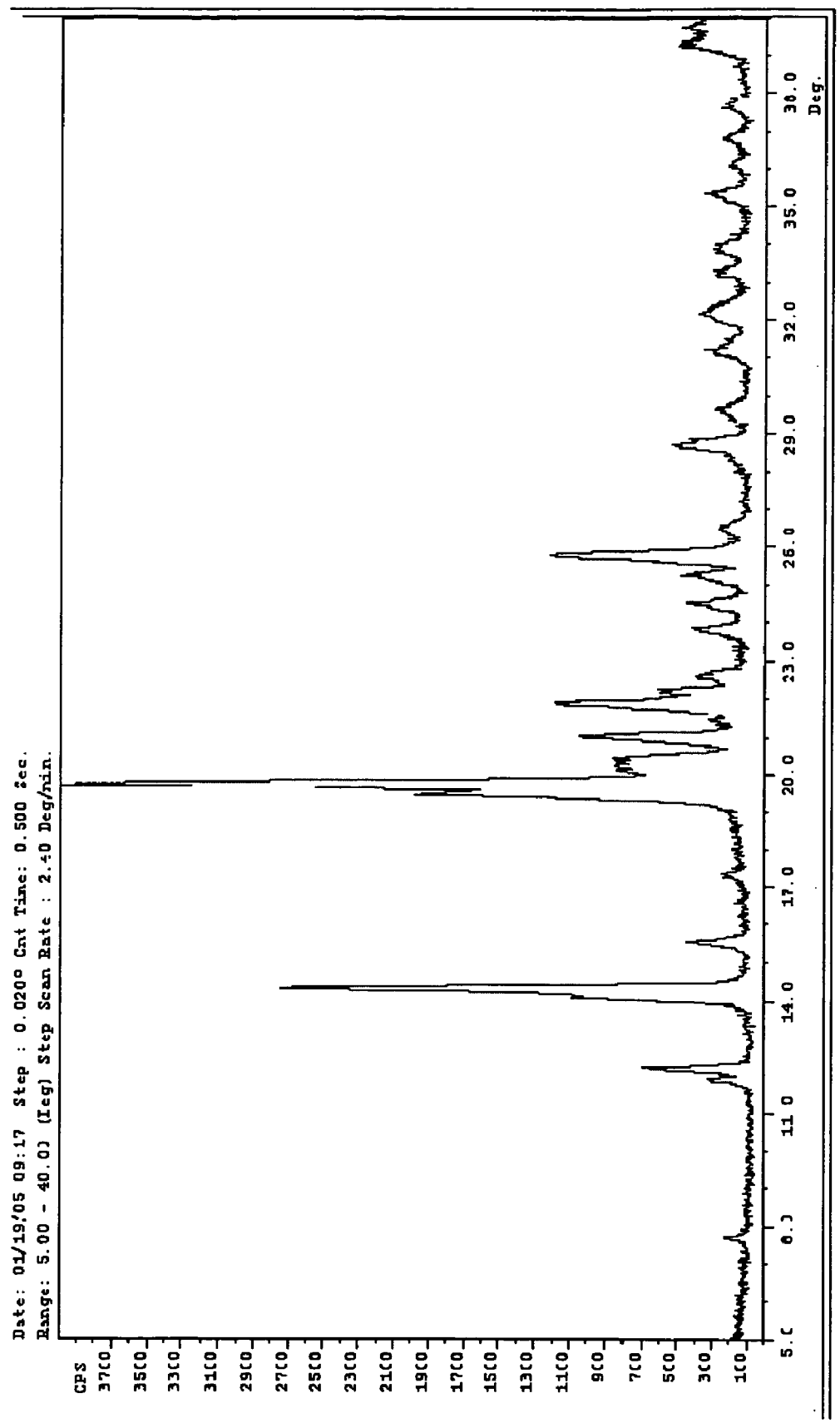
FIG. 1 provides an X-ray powder diffraction of 4-[2-dimethylamino-1-(4-phenyl)-ethyl-tetrahydro-pyran-4-ol.
Figure 2:
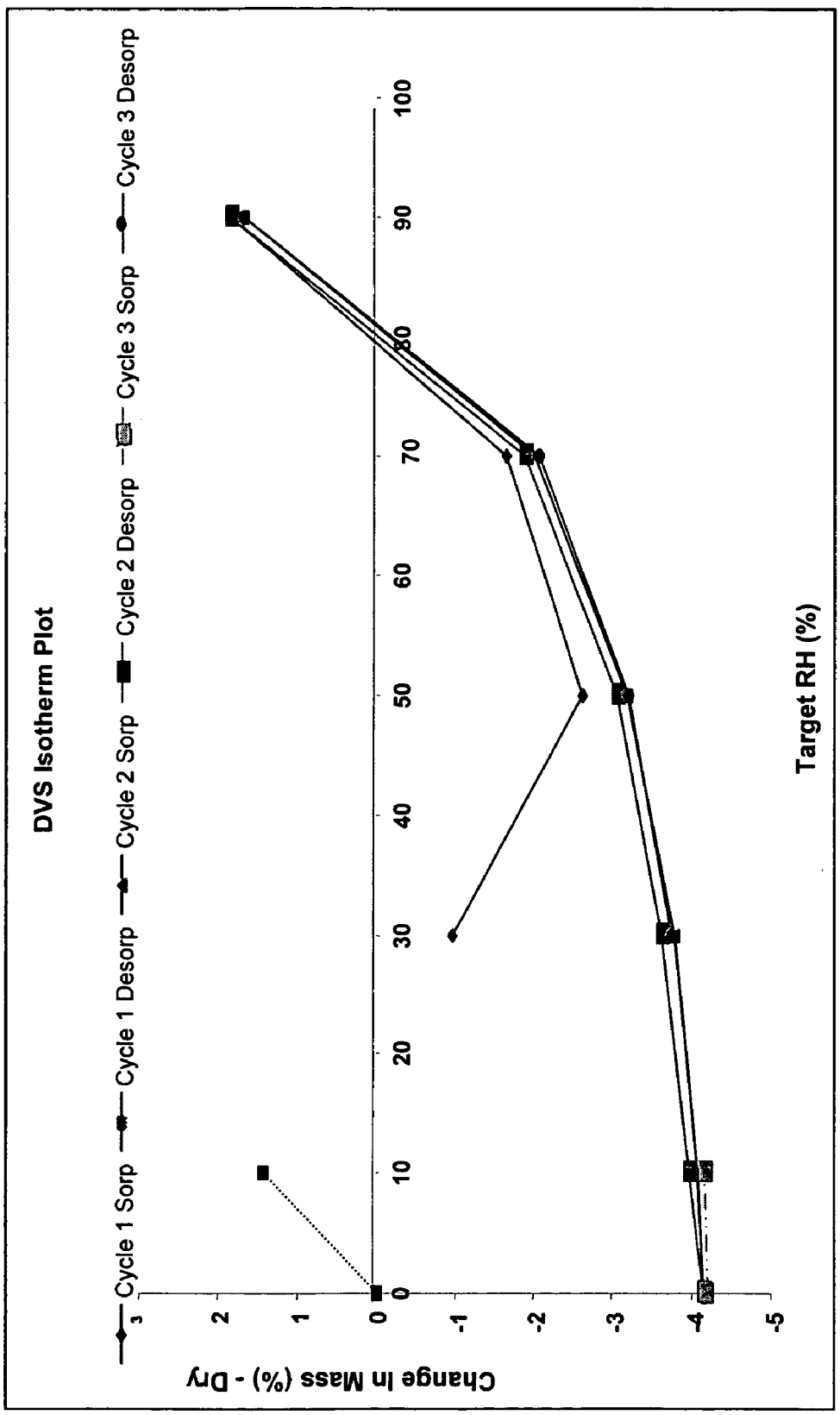
FIG. 2 provides a chart of the hygroscopicity profile of 4-[2-dimethylamino-1-(4-phenyl)-ethyl-tetrahydro-pyran-4-ol.
Figure 3:
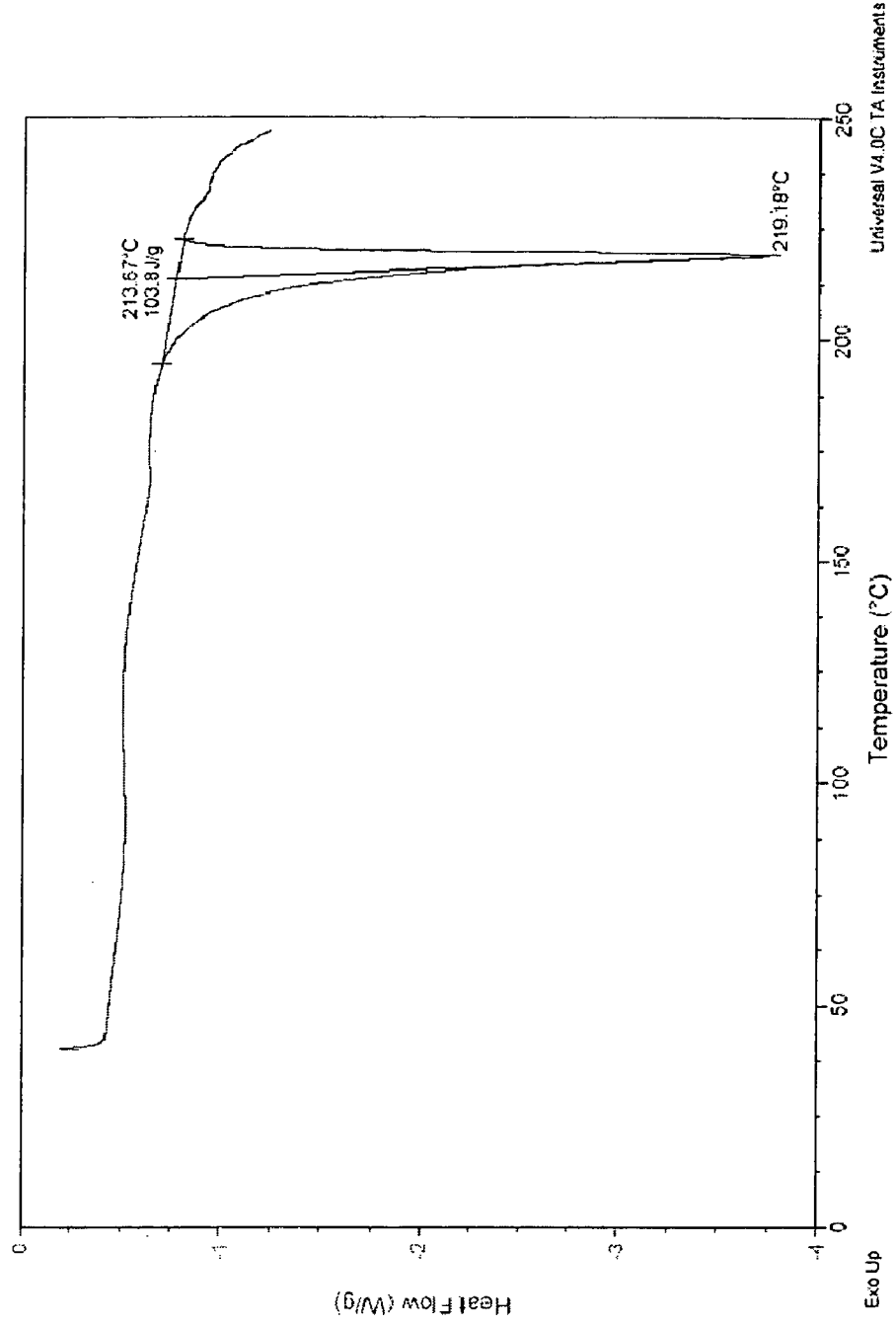
FIG. 3 provides a chart of the DSC of 4-[2-dimethylamino-1-(4-phenyl)-ethyl-tetrahydro-pyran-4-ol.
Figure 4:
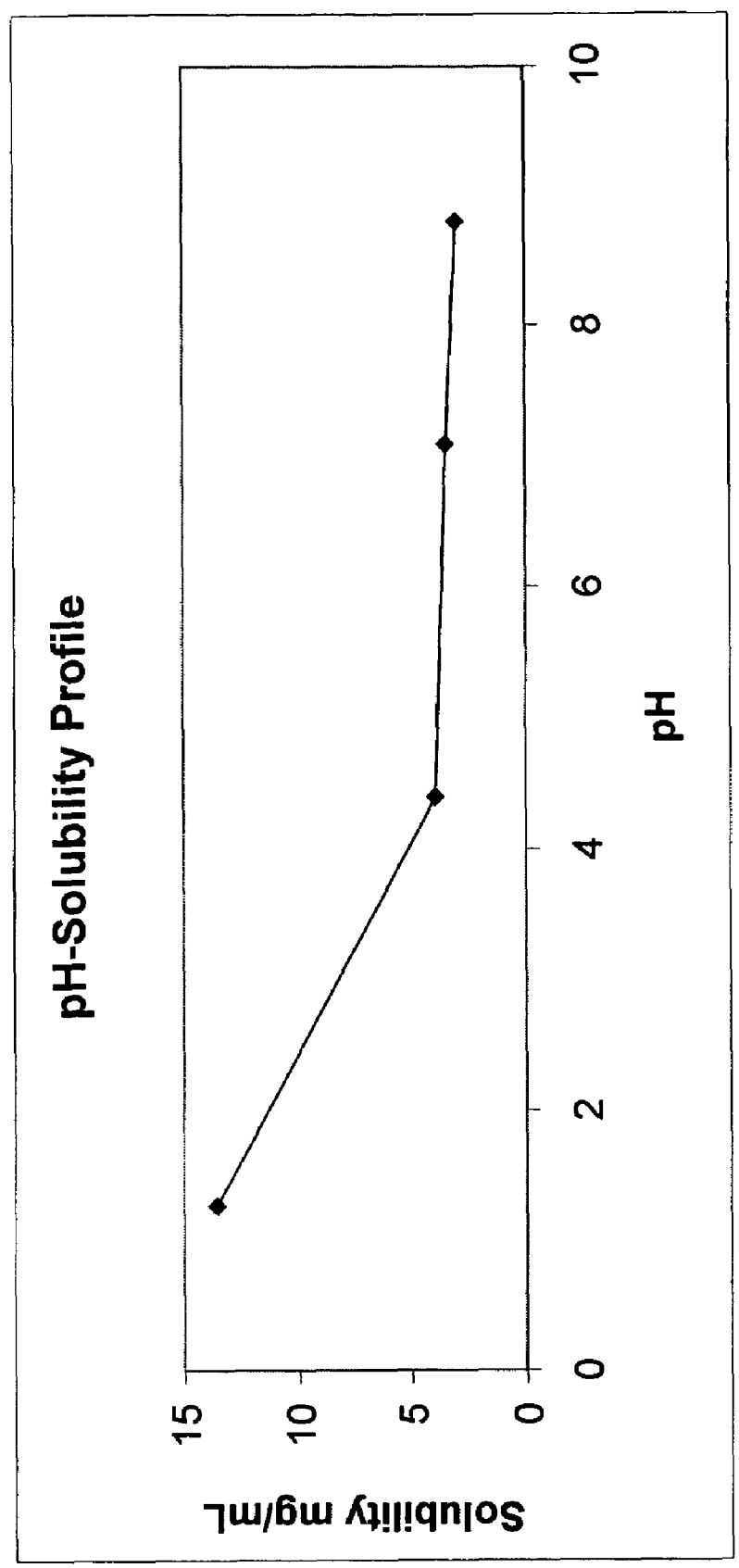
FIG. 4 provides a chart of the pH - solubility profile of 4-[2-dimethylamino-1-(4-phenyl)-ethyl-tetrahydro-pyran-4-ol.

The present invention provides a compound which has the structure:

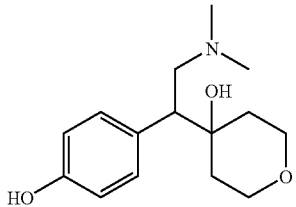

or a prodrug or a pharmaceutically acceptable salt thereof.

Advantageously, compounds and formulations described herein reduce the undesirable side-effects of SNRI's, including constipation, hypertension, and the histamine-related side-effects. The compounds described herein are also predicted to have low norepinephrine reuptake inhibition activity (NE), as compared to existing SNRI's. This attribute is very attractive for SNRI indications, e.g., depression, for patients that have cardiovascular risks related to hypertension. The compounds will have activity on serotonin and norepinephrine neurotransmitters in the brain making it desirable for anti-depression therapy and other related neurological indications.

In one embodiment, a compound of the above structure may contain one or more asymmetric carbon atoms and some of the compounds may contain one or more asymmetric (chiral) centers and may thus give rise to optical isomers and diastereomers. Thus, in one embodiment, the invention includes such optical isomers and diastereomers; as well as the racemic and resolved, enantiomerically pure stereoisomers; as well as other mixtures of the R and S stereoisomers, and pharmaceutically acceptable salts, hydrates, and prodrugs thereof.

The term "alkyl" is used herein to refer to both straight- and branched-chain saturated aliphatic hydrocarbon groups, generally of 1, 2, 3, 4, 5, 6, 7 or 8 carbon atoms in length, unless otherwise specified. The term "lower alkyl" is used to refer to alkyl chains of 1, 2, 3, or 4 carbons in length. The terms "substituted alkyl" refers to alkyl as just described having from one to three substituents selected from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl group provided that the attachment constitutes a stable chemical moiety.

The term "halogen" refers to Cl, Br, F, or I.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, and phenanthryl.

The term "substituted aryl" refers to aryl as just defined having one, two, three or four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

Alkenyl and alkynyl groups may have for example 2 to 7 carbon atoms. Cycloalkyl groups may have 3 to 8 carbon atoms.

The term "heterocyclic" is used herein to describe a stable 4-, 5-, 6- or 7-membered monocyclic or a stable multicyclic heterocyclic ring which is saturated, partially unsaturated, or unsaturated, and which consists of carbon atoms and from one to four heteroatoms selected from the group including N, O, and S atoms. At least one carbon atom may be C=O. The N and S atoms may be oxidized. The heterocyclic ring also includes any multicyclic ring in which any of above defined heterocyclic rings is fused to an aryl ring. A multicyclic ring may be 2 or 3 monocyclic rings of 4- to 7-membered rings as described above. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one to four substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio.

The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom.

The compounds of the present invention can be used in the form of salts derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include salts with alkali metals or alkaline earth metals, such as sodium (e.g., sodium hydroxide), potassium (e.g., potassium hydroxide), calcium or magnesium.

These salts, as well as other compounds of the invention may be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

SYNTHESIS

The compounds of the present invention can be prepared using the methods described herein, together with synthetic methods known in the synthetic organic arts or variations of these methods by one of skill in the art. The compounds of the present invention can be prepared using the methods described below, together with synthetic methods known in the synthetic organic arts or variations of these methods. [See, generally, *Comprehensive Organic Synthesis*, "Selectivity, Strategy & Efficiency in Modern Organic Chemistry", ed., I. Fleming, Pergamon Press, New York (1991); *Comprehensive Organic Chemistry*, "The Synthesis and Reactions of Organic Compounds", ed. J. F. Stoddard, Pergamon Press, New York (1979)]. The following scheme provides one method for the synthesis of a compound of the invention.

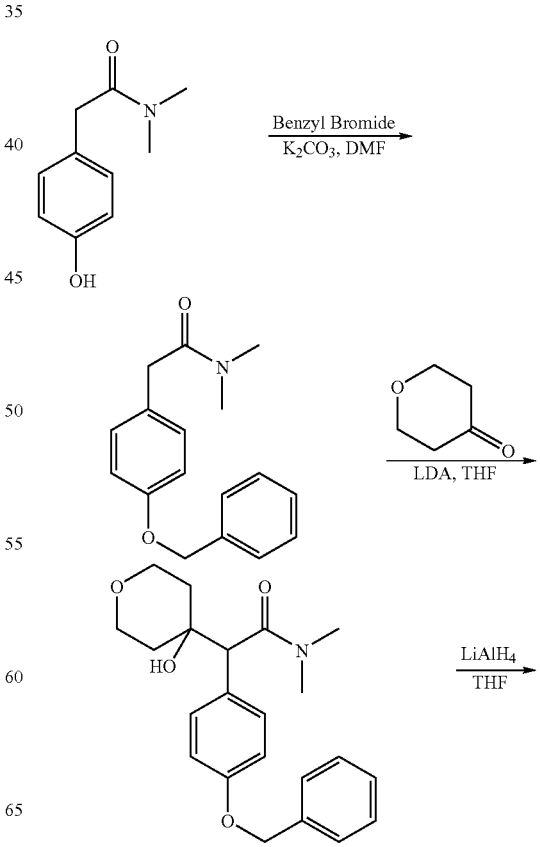

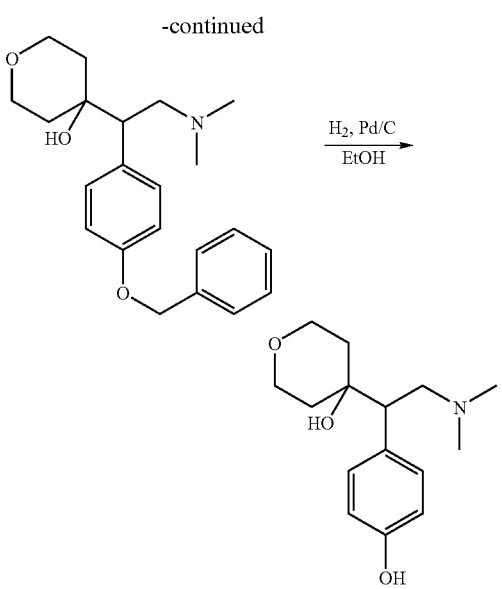

In another embodiment, a method of preparing a compound of structure A can be used:

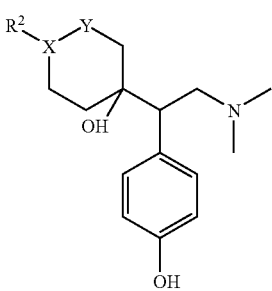

wherein X is C, N, or O; and Y is a C or absent; when X is C; R² is selected from H, halogen, CF₃, phenyl, SCH₃, NHCH₃, OC₁-C₆ alkyl, and substituted OC₁-C₆alkyl; and when X is N, R² is selected from H, phenyl or CF₃.

This method involves the step of reacting a 2-(4-hydroxyphenol)-dimethylacetamide with a benzyl halide to afford a 2-(4-benzyloxy-phenyl)-dimethylacetamide. The 2-(4-hydroxy-phenol)-dialkylacetamide may be in a solution comprising dimethylformamide. Further, the solution can be treated with potassium carbonate prior to reaction with the benzyl halide.

To prepare the compound of structure A, the 2-(4-benzyloxy-phenyl)-dimethylacetamide is reacted with a compound having the structure:

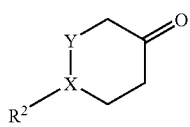

wherein X is C, N, or O; and Y is a C or absent; when X is C; R² is selected from H, halogen, CF₃, SCH₃, NHCH₃, OH, OC₁-C₆ alkyl, phenyl, and substituted OC₁-C₆alkyl; when X is N, R² is H, phenyl or CF₃; in a solution (e.g., containing THF) with a suitable base. Examples of suitable bases include, e.g., lithium diisopropylamide and isopropyl magnesium bromide. In one embodiment, this compound is selected from the group consisting of pyran-4-one and phenyl-piperidine-4-one. The resulting product is reduced (e.g., using LiAlH₄) to provide the corresponding dimethylamine and the benzyl ether is hydrogenated to remove the benzyl group and afford a compound of structure A.

Advantageously, it has been found that the process is highly selective for the cis-compounds, leading to a high yield and good crystallinity. Without wishing to be bound by theory, it is believed that the LAH reaction plays a significant role in this specificity.

In one embodiment, the method of synthesizing the compounds described herein provides a compound having a configuration is greater than 50% cis diastereomer. In another embodiment, the method of synthesizing the compounds of the invention provides a compound having the configuration which is greater than 95% cis diastereomer. In another embodiment, it may be desirable to substitute sodium borohydride for the LAH.

In one embodiment, 4-(Dimethylcarbamoylmethyl)phenol in dimethylformamide (DMF) is treated with K₂CO₃ followed by benzyl bromide. The benzyl bromide protecting group is particularly well suited for use in the method of synthesizing the compounds of the invention because of its ease of removal during the final step. However, other protecting groups may be substituted.

The mixture is stirred at room temperature followed by heating at 60° C. for 1 hour. The mixture is concentrated to remove DMF, diluted with EtOAc and washed with water. Dry MgSO₄ is added, the mixture filtered and concentrated to low volume. Hexane is added to precipitate the ketal intermediate product. Solids are collected via filtration and dried.

A solution of the amide a pyran-4-one in THF, a solution of LDA, and a solution of pyran-4-one in THF are mixed. The reaction is quenched with saturated NH₄Cl, extracted with EtOAc and concentrated to an oil. Product is crystallized from hot EtOAc/hexanes to provide the ketone intermediate.

A solution of the ketone in THF was added to a solution of lithium aluminum hydride (LAH) in THF at −78° C. The mixture is warmed to room temperature and stirred for at least 3 hours. The reaction is quenched with MeOH followed by NaOH and stirred. The solid are removed by filtration, followed by a wash (e.g., with THF), and concentrated to give a solid. The resulting solid is recrystallized from EtOAc/hexanes to provide the corresponding benzyl ether.

This process is anticipated to be highly selective for the cis-compounds, leading to a high yield and good crystallinity. Without wishing to be bound by theory, it is believed that the LAH reaction plays a significant role in this specificity. In one embodiment, the method of synthesizing the compounds of the invention provides a compound having a configuration is greater than 50% cis diastereomer. In another embodiment, the method of synthesizing the compounds of the invention provides a compound having the configuration which is greater than 95% cis diastereomer. In another embodiment, it may be desirable to substitute sodium borohydride for the LAH.

A mixture of the benzyl ether and Pd/C in 100 mL of SDA alcohol are hydrogenated under pressure overnight. The solid is purified by filtration followed by an ethanol wash. Solid is concentrated and crystallized from EtOAc/hexane to give the final product.

Salts may be formed by contacting stoichiometric amounts of the acid with the free base. Alternatively, the acid may be used in excess, usually no more than 1.5 equivalents. In one embodiment, the base or the acid are in solution, or both are in solution.

The crystalline salt may be prepared by directly crystallizing from a solvent. Improved yield may be obtained by evaporation of some or all of the solvent or by crystallization at elevated temperatures followed by controlled cooling, preferably in stages. Careful control of precipitation temperature and seeding may be used to improve the reproducibility of the production process and the particle size distribution and form of the product.

USE OF THE COMPOUNDS OF INVENTION

In one embodiment, compounds of the invention provide a different ratio of serotonin reuptake inhibition to norepinephrine reuptake inhibition than the currently available SNRI's. This attribute is very attractive for indications like Irritable Bowel Syndrome (IBS) where the higher NE activity of SNRI's limits the application because of constipation side effects. This lower NE activity is also attractive for patients that have cardiovascular risks related to the side effect of hypertension. It also has an application in dealing with urinary incontinence.

The compositions can be used to treat or prevent central nervous system disorders including, but not limited to, depression (including but not limited to, major depressive disorder, bipolar disorder and dysthymia), anxiety, fibromyalgia, anxiety, panic disorder, agorophobia, post traumatic stress disorder, premenstrual dysphoric disorder (also known as premenstrual syndrome), attention deficit disorder (with and without hyperactivity), obsessive compulsive disorder (including trichotillomania), social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, (including premature ejaculation), borderline personality disorder, chronic fatigue syndrome, incontinence (including fecal incontinence, overflow incontinence, passive incontinence, reflex incontinence, stress urinary incontinence, urge incontinence, urinary exertional incontinence and urinary incontinence), pain (including but not limited to migraine, chronic back pain, phantom limb pain, central pain, neuropathic pain such as diabetic neuropathy, and postherpetic neuropathy), Shy Drager syndrome, Raynaud's syndrome, Parkinson's Disease, epilepsy, and others. Compounds and compositions can also be used for preventing relapse or recurrence of depression; to treat cognitive impairment; for the inducement of cognitive enhancement in patient suffering from senile dementia, Alzheimer's disease, memory loss, amnesia and amnesia syndrome; and in regimens for cessation of smoking or other tobacco uses. Additionally, compounds and compositions can be used for treating hypothalamic amenorrhea in depressed and non-depressed human females.

An effective amount of the composition is an amount sufficient to prevent, inhibit, or alleviate one or more symptoms of the aforementioned conditions. The dosage amount useful to treat, prevent, inhibit or alleviate each of the aforementioned conditions will vary with the severity of the condition to be treated and the route of administration. The dose, and dose frequency will also vary according to age, body weight, response and past medical history of the individual human patient. In generally the recommended daily dose range for the conditions described herein lie within the range of 10 mg to about 1,000 mg per day, or within the range of about 15 mg to about 350 mg/day or from about 15 mg to about 140 mg/day. In other embodiments of the invention, the dosage will range from about 30 mg to about 90 mg/day. Dosage is described in terms of the free base and is adjusted accordingly for the succinate salt. In managing the patient, the therapy is generally initiated at a lower dose and increased if necessary. Dosages for non-human patients can be adjusted accordingly by one skilled in the art.

A compound may also be provided in combination with other active agents including, e.g., venlafaxine. The dosage of venlafaxine is about 75 mg to about 350 mg/day or about 75 mg to about 225 mg/day. In another embodiment, the dosage of venlafaxine is about 75 mg to about 150 mg/day. Venlafaxine or another active agent delivered in a regimen with the composition of the invention may be formulated together with the composition of the invention, or delivered separately.

Any suitable route of administration can be employed for providing the patient with an effective amount of a compound of the invention. For example, oral, mucosal (e.g., nasal, sublingual, buccal, rectal or vaginal), parental (e.g. intravenous or intramuscular), transdermal, and subcutaneous routes can be employed. Preferred routes of administration include oral, transdermal and mucosal.

A compound of the invention can be combined with a pharmaceutical carrier or excipient (e.g., pharmaceutically acceptable carriers and excipients) according to conventional pharmaceutical compounding technique to form a pharmaceutical composition or dosage form. Suitable pharmaceutically acceptable carriers and excipients include, but are not limited to, those described in Remington's, The Science and Practice of Pharmacy, (Gennaro, A R, ed., 19th edition, 1995, Mack Pub. Co.), which is herein incorporated by reference. The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human).

COMPOSITIONS

In one embodiment, the composition of the invention is an immediate release formulation. In another embodiment, the composition of the invention is a sustained release formulation. Illustrative formulations are described herein. However, the invention is not so limited.

Still other suitable compositions of the invention will be readily apparent to one of skill in the art given the information provided herein. For example, in addition to providing dosing units suitable for oral administration such as tablets, capsules and caplets, the invention provides dosing units suitable for parenteral administration, transdermal or mucosal administration.

Oral solid pharmaceutical compositions may include, but are not limited to starches, sugars, microcrystalline cellulose, diluents, granulating agents, lubricants, binders and disintegrating agents. In one embodiment, the pharmaceutical composition and dosage form may also include other active components.

In one embodiment, the active component(s) are prepared in the form of a tablet or tablet-in-capsule. For example, a compound is mixed with suitable excipients to form a granulation. In one embodiment, the granulation is formed using a roller compactor. In another embodiment, the granulation is formed using a high shear granulator. However, other methods known to those of skill in the art, including, e.g., a low shear granulator, a blender, etc, can be utilized to prepare suitable granulations. The granulation is then compressed using conventional methods to form a tablet.

This tablet may be provided with additional layers, optionally, containing additional layers with active components, or other layers as may be desired for enteric coating, seal coating, separation between layers, or the like. In one embodiment, the tablet core contains one active component and a second active component is provided in a coating layer.

Optionally, a final seal coat is applied over the tablet. Suitably, this final seal coat is composed of hydroxypropylmethylcellulose (HPMC) and water, upon drying, is less than about 1 wt % of the total, coated tablet. Optionally, talc is utilized as a final step prior to filling the multi-layer tablets into a suitable packaging unit.

Alternatively or additionally, the tablet may be loaded into a capsule.

In another aspect, the invention provides a capsule containing the active component. Such capsules are produced using techniques known to those of skill in the art.

In one embodiment, the invention provides a formulation containing a core of one or more of the compounds of the invention and one or more pharmaceutically acceptable excipients, e.g., diluents, binders, fillers, glidants, anti-adherents, a pH adjuster and/or an adjuvant. The core contains about 3% w/w to about 70% w/w active compound(s). In other embodiments, the compound can range from about 5% w/w to about 60% w/w, from about 10% w/w to about 50% w/w, from about 20% w/w to about 40% w/w, or from about 25% w/w to about 35% w/w, about 30% w/w to about 45% w/w, or about 32% to about 44% w/w, based upon 100% weight of the uncoated dosage form. The core may be in a sustained release formulation or other suitable cores as are described in greater detail below may be selected. In one embodiment, a delay release coat and/or an enteric coat are provided over the core.

Suitably, the total amount of diluent, binders, fillers, glidants, anti-adherents, and adjuvants present in the core is an amount of about 30% w/w to about 97% w/w of the core, or about 25 wt % to about 80 wt % of the core. For example, when present, a binder, diluent and/or filler can each be present in an amount of about 15% w/w to about 80% w/w, or about 20% w/w to about 70% w/w, or about 25% w/w to about 45% w/w, or about 30% w/w to about 42% w/w of the uncoated dosage form. The total amount of a pH adjuster in the formulation can range from about 0.1% w/w to about 10% w/w of the core, or about 1% w/w to about 8% w/w, or about 3% w/w to about 7% w/w. However, these percentages can be adjusted as needed or desired by one of skill in the art.

The binder may be selected from among known binders, including, e.g., cellulose, and povidone, among others. In one embodiment, the binder is selected from among microcrystalline cellulose, crospovidone, and mixtures thereof.

Suitable pH adjusters include, e.g., sodium carbonate, sodium bicarbonate, potassium carbonate, lithium carbonate, among others. Still other suitable components will be readily apparent to one of skill in the art.

In one embodiment, the compound(s) of the invention is in a sustained release formulation which contains rate-controlling components. Typically, such rate controlling components are rate controlling polymers selected from among hydrophilic polymers and inert plasticized polymers. Suitable rate controlling hydrophilic polymers include, without limitation, polyvinyl alcohol (PVA), hypomellose and mixtures thereof. Examples of suitable insoluble or inert "plastic" polymers include, without limitation, one or more poly-methacrylates (i. e., Eudragit®polymer). Other suitable rate-controlling polymer materials include, e.g., hydroxyalkyl celluloses, poly(ethylene) oxides, alkyl celluloses, carboxymethyl celluloses, hydrophilic cellulose derivatives, and polyethylene glycol.

In one embodiment, a formulation of the invention contains about 5% w/w to about 75% w/w microcrystalline cellulose (MCC), about 10% w/w to about 70% w/w MCC, about 20% w/w to about 60% w/w, about 25 wt % to about 30 wt %, or about 30% w/w to about 50% w/w, based on the weight of the uncoated dosage unit.

In one embodiment, the core is uncoated. These cores can be placed into a suitable capsule shell or compressed into tablets, using techniques know to those of skill in the art. Suitably, the results capsule shell or compressed tablets contain 10 mg to 400 mg of active compound.

In other embodiments, the formulation can contain one or more coatings over the core. In still other embodiments, the formulation consists of a pellet core and non-functional seal coating and a functional second coating.

In one embodiment, an initial seal coat can be applied directly to the core. Although the components of this seal coat can be modified by one of skill in the art, the seal coat may be selected from among suitable polymers such as hydroxypropyl methylcellulose (HPMC), ethylcellulose, polyvinyl alcohol, and combinations thereof, optionally containing plasticizers and other desirable components. A particularly suitable seal coat contains HPMC. For example, a suitable seal coat can be applied as a HPMC solution at a concentration of about 3% w/w to 25% w/w, and preferably 5% w/w to about 7.5% w/w. The initial seal coat can be applied on a fluid bed coater, e.g., by spraying. In one embodiment, an Aeromatic Strea™ fluid bed apparatus can be fitted with a Wurster column and bottom spray nozzle system. Approximately 200 grams of the dried pellet cores are charged into the unit. The Opadry® Clear seal coat is applied with an inlet temperature of approximately 50° C. to 60° C., a coating solution spray rate of 5 to 10 grams/minute, atomization pressure of 1 to 2 bar. Upon drying, under suitable conditions, the initial seal coat is in the range of about 1% w/w to about 3% w/w, or about 2% w/w, of the uncoated core. In another embodiment, a commercially available seal coat containing HPMC, among other inert components, is utilized. One such commercially available seal coat is Opadry® Clear (Colorcon, Inc.).

In one embodiment, the oral dosage unit contains a further release or "delay" coating layer. This release coating layer may be applied over an initial seal coat or directly over a core. In one embodiment, the release coat contains an ethylcellulose-based product and hypomellose. An example of one suitable ethylcellulose-based product is an aqueous ethylcellulose dispersion (25% solids). One such product is commercially available as Surelease® product (Colorcon, Inc.). In one embodiment, a solution of an aqueous ethylcellulose (25% solids) dispersion of about 3% w/w to about 25% w/w, and preferably about 3% to about 7%, or about 5% w/w, is applied to the core. Optionally, hypomellose, e.g., in an amount of about 5 to 15% by weight, and preferably, about 10% by weight, is mixed with the ethylcellulose dispersion, to form the coat solution. Thus, such the ethylcellulose may be about 85% to about 95%, by weight, or in embodiment, about 90% by weight, of the coat solution. Upon drying under suitable conditions, the total release coat is in the range of about 2% to about 5%, or about 3% to about 4% w/w of the uncoated or initially-coated core.

An enteric coat (rate-controlling film) may be applied to the multiparticulates and may include, but is not limited to polymethacrylates, hypomellose, and ethylcellulose, or a combination thereof. The modified release multiparticulate formulation can contain from about 3% w/w to about 70% w/w of active compound or a combination thereof, and from about 5% w/w to about 75% w/w microcrystalline cellulose, based on the weight of an uncoated dosage form.

In one embodiment, the enteric coat contains a product which is a copolymer of methacrylic acid and methacrylates, such as the commercially available Eudragit® L 30 K55 (Röhm GmbH & Co. KG). Suitably, this enteric coat is applied such that it coats the multiparticulate in an amount of about 15 to 45% w/w, or about 20% w/w to about 30% w/w, or about 25% w/w to about 30% w/w of the uncoated or initially-coated multiparticulate. In one embodiment, the enteric coat is composed of a Eudragit® L30D-55 copolymer (Röhm GmbH & Co. KG), talc, triethyl citrate, and water. More particularly, the enteric coating may contain about 30% w/w of a 30 wt % dispersion of Eudragit® L 30 D55 coating; about 15% w/w talc, about 3% triethyl citrate; a pH adjuster such as sodium hydroxide and water.

In another embodiment, the enteric coat contains an ethylcellulose-based product, such as the commercially available Surelease® aqueous ethylcellulose dispersion (25% solids) product (Colorcon, Inc.). In one embodiment, a solution of Surelease® dispersion of about 3% w/w to about 25% w/w, and preferably about 3% to about 7%, or about 5% w/w, is applied to the multiparticulate. Upon drying under suitable conditions, the enteric coat is in the range of about 2% to about 5%, or about 3% to about 4% w/w of the uncoated or initially-coated core.

The enteric coat can be applied directly to the uncoated core, i.e., the uncoated core, or may be applied over an initial seal coat. The enteric coat, as described above, is typically applied on a fluid bed coater. In one embodiment, Surelease® aqueous ethylcellulose dispersion (25% solids) is applied in a similar fashion as the seal coat. After the ethylcellulose coat is applied, the core is dried for an additional 5 to 10 minutes.

In one embodiment, a final seal coat is applied over the enteric coat and, optionally, talc is utilized as a final step prior to filling the formulations into a suitable packaging unit. Suitably, this final seal coat is composed of HPMC and water, upon drying, is less than about 1 wt % of the total, coated oral dosage unit.

Kits

In another embodiment, the present invention provides products containing the compounds and compositions of the invention.

In one embodiment, the compositions are packaged for use by the patient or his caregiver. For example, the compositions can be packaged in a foil or other suitable package and is suitable for mixing into a food product (e.g., applesauce or the like) or into a drink for consumption by the patient.

In another embodiment, the compositions are suspended in a physiologically compatible suspending liquid. For oral liquid pharmaceutical compositions, pharmaceutical carriers and excipients can include, but are not limited to water, glycols, oils, alcohols, flavoring agents, preservatives, coloring agents, and the like.

In yet another embodiment, the compositions are filled in capsules, caplets or the like for oral delivery.

In another embodiment, the present invention provides for the use of compositions of the invention in the preparation of medicaments, including but not limited to medicaments useful in the treatment of depression, gastrointestinal side-effects of venlafaxine in a subject undergoing treatment therewith, and irritable bowel syndrome.

In another embodiment, the present invention provides for the use of multiparticulate formulations of the invention in the preparation of medicaments for delivery to a pediatric or geriatric patient.

In other embodiments, the present invention provides for the use of multiparticulate formulations of the invention in the preparation of dosing units, including but not limited to dosing units for oral, transdermal, or mucosal administration.

Also encompassed by the invention are pharmaceutical packs and kits comprising a container, such as a foil package or other suitable container, having a formulation of the invention in unit dosage form.

The following examples are illustrative of the invention.

EXAMPLE 1

Production 4-[2-Dimethylamino-1-(4-Hydroxy-Phenyl)-ethyl]-Tetrahydro-Pyran-4-ol

The above-identified compound may be synthesized according to the following scheme.

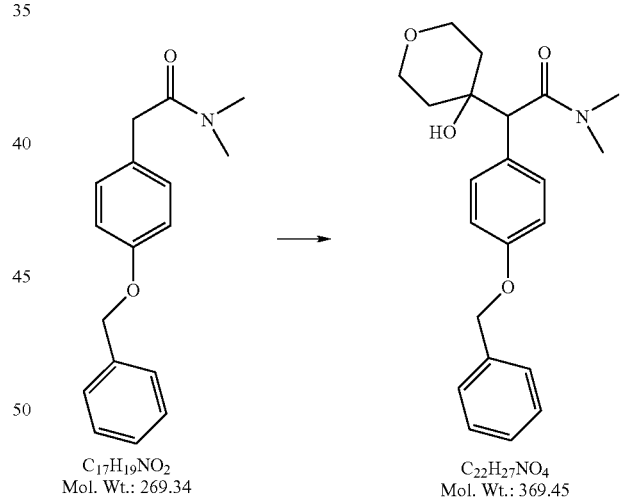

C$_{17}$H$_{19}$NO$_2$
Mol. Wt.: 269.34

C$_{22}$H$_{27}$NO$_4$
Mol. Wt.: 369.45

A solution of the amide (3 g, 11.1 mmol) in 40 mL of THF was added to a solution of 2 N LDA (9 mL, 18 mmol) at −78° C. After 1 h a solution of pyran-4-one (1.5 g, 15 mmol) in 15 mL of THF were added. After 2 h the mixture was quenched with sat. NH4Cl. The layers were separated and the aqueous layer was extracted with EtOAc. The combined organic layers were concentrated, diluted with CH2Cl2, washed with water, dried Na2SO4, filtered and concentrated to give an oil which solidified upon standing. Trituration with EtOAc/hexane gave 2.88 g, 70% yield of an off-white solid. HPLC/MS 98.6 area% with 1.4 area % SM amide.

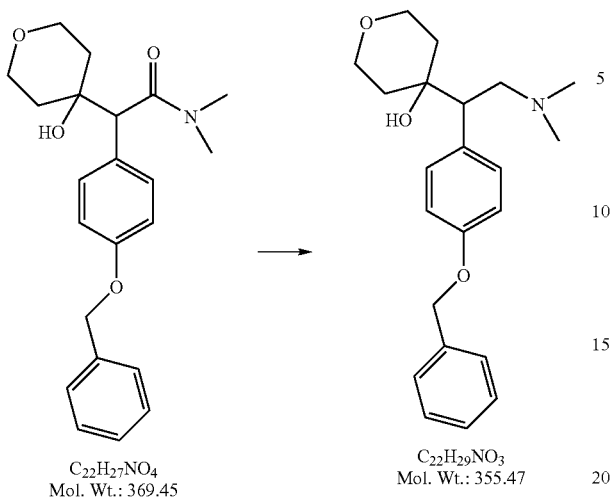

C$_{22}$H$_{27}$NO$_4$
Mol. Wt.: 369.45

C$_{22}$H$_{29}$NO$_3$
Mol. Wt.: 355.47

A solution of amide (2 g, 5.4 mmol) in 25 mL of THF was added to a solution of 1M LAH (19 mL, 19 mmol) in THF at −78° C. Allow to slowly warm to RT and stir overnight. Quench with MeOH (5 mL) followed by 1N NaOH (10 mL). Stir for 20 minutes before filtering off solids and washing with THF. The combined THF parts were concentrated, diluted with CH$_2$Cl$_2$, washed with water, dried Na$_2$SO$_4$, filtered and concentrated. Trituration with EtOAc/hexanes gave 1.27 g, 66% yield of a solid. LC/MS showed 96.2 area % desired material.

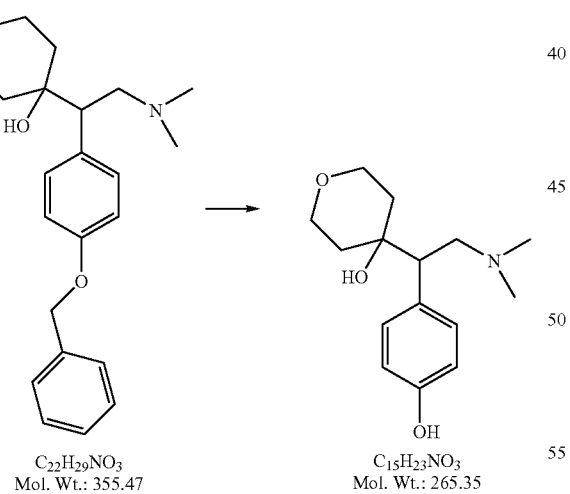

C$_{22}$H$_{29}$NO$_3$
Mol. Wt.: 355.47

C$_{15}$H$_{23}$NO$_3$
Mol. Wt.: 265.35

The benzyl ether (1 g, 2.81 mmol) in 25 mL of 2B-3 SDA alcohol and 250 mg of 10% Pd/C (50% wet) were hydrogenated at 130 psi overnight. Filter off catalyst and concentrate to give an oil. Trituration with EtOAc/hexane gave 332.9 mg, 45% yield of a tan solid of the title compound. LC/MS 96.9 area%.

EXAMPLE 2

Physical-Chemical Properties of 4-[2-Dimethylamino1-(4-Hydroxy-Phenyl)-ethyl]-Tetrahydro-Pyran-4-ol

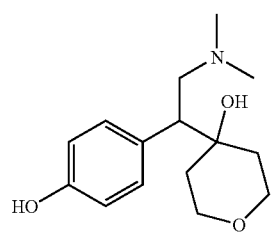

Purity HPLC/MS shows 96.9 area % with SLI 0.7 area %
Molecular Formula C$_{15}$H$_{23}$NO$_3$
Molecular Weight 265.35
Appearance light brown crystalline powder
Melting point (DSC onset) 213.67° C.
X-ray (powder diff) Crystalline
Hygroscopicity Non-hygroscopic (2% weight gain @ 70% RH, 6% weight gain @ 90% RH, weight gain was lost when returned to 10% RH or 0% RH),
Solution Stability The compound was stable for at least 24 hours at room temperature in all of the aqueous solutions (pH 1.25-8.8).
pH-Solubility Final pH 1.25 13.57 mg/ml
Final pH 4.40 3.91 mg/ml
Final pH 7.10 3.47 mg/ml
Final pH 8.80 2.96 mg/ml

EXAMPLE 3

Permeability Assessment of Compounds of Invention Hts-24 Caco-2 Model

The rate of drug transport through the caco-2 cells can be determined as the Apparent Permeability Coefficient according to the following formula:

$$P_{app} = \frac{\Delta Q}{\Delta T} \times \frac{Rv \, \text{cm} \cdot s^{-1}}{60 \cdot A \cdot C_o}$$

$\Delta Q$=Change in quantity
$\Delta T$=Change in time (minutes)
$C_o$=Initial conc$_n$ in the donor chamber (mM·cm$^{-3}$)
A=Surface area of membrane (cm$^2$)
60=Conversion factor to give cm·s$^{-1}$
Rv=volume of receiver compartment.

Transepithelial electrical resistance (TER) is calculated from resistance measurements according to the following formula: TER=(R[cells+filter+medium])−(R[filter+medium])×cell area.

Apparent permeability rates are interpreted as follows. Apparent permeability values which are equal to or greater than those observed for metoprolol or propranolol during the same assay run are considered to give a predicted fraction absorbed estimate of ≧90% (high permeability classification). Apparent permeability values less than metoprolol or propranolol are considered to be ≦90% fa (moderate permeability classification). Apparent permeability values of <10 nms⁻¹ are considered to be ≦50% fa (low permeability classification). TER values of <120 ohms cm² indicate low monolayer integrity over the assay period.

A compound/metoprolol or propranolol ratio of ≧1 indicates a high permeability compound. A compound/metoprolol or propranolol ratio of <1 indicates a moderate to low permeability compound.

EXAMPLE 4

Pharmacology

In initial experiments using in-house assays, 4-[2-dimethylamino-1-(4-hydroxy-phenyl)-ethyl]-tetrahydro-pyran-4-ol has been found active in a human serotonin transporter assay.

Other receptor assay binding studies can be conducted in accordance with published and commercially available assays. These assays can be performed as described in the following publications, as modified by Novascreen™ services. The receptor binding assays can include, e.g., Adrenergic α-2A (human) binding assay [D. B. Bylund et al, *J Pharmacol & Exp Ther*, 245(2):600-607 (1988), with modifications; J A Totaro et al, *Life Sciences*, 44:459-467 (1989)]; dopamine transporter binding assay [Madras et al, *Mol. Pharmacol.*, 36:518-524, with modifications, J J Javitch et al, *Mol Pharmacol*, 26:35-44 (1984)]; histamine H1 binding assay [Chang, et al., *J Neurochem*, 32:1658-1663 (1979), with modifications, J I Martinez-Mir, et al., *Brain Res*, 526:322-327 (1990); E E J Haaksma, et al, *Pharmacol Ther*, 47:73-104 (1990)]; imidazoline binding assay [C M Brown et al, *Brit. J Pharmacol*, 99(4):803-809 (1990), with modifications], muscarinic M5 (human recombinant) binding assay [N J Buckley et al, *Mol Pharmacol*, 35:469-476 (1989), with modifications]; norepinephrine transporter (human recombinant) binding assay [R. Raisman, et al., *Eur J Pharmacol*, 78:345-351 (1982), with modification, S. Z. Raisman, et al, *Eur J Pharmacol*, 72:423 (1981)]; serotonin transporter (human) binding assay [R J D'Amato, et al, *J Pharmacol & Exp Ther*, 242:364-371 (1987), with modifications; NL Brown et al, *Eur J Pharmacol*, 123:161-165 (1986)]. The cellular/functional assays include, e.g., the norepinephrine transport (NET-T) human [A. Galli, et al, *J Exp Biol*, 198:2197-2212 (1995); and the serotonin transport (Human) assay [D'Amato et al, cited above and NL Brown et al, *Eur J Pharmacol*, 123:161-165 (1986)]. The results are shown in % Inhibition of the receptor. Venlafaxine has been described as having a 20% inhibition of Histamine H1 at 101M (Muth et al., *Drug Development Research* 23:191-199 (1991)).

It is anticipated that the compounds of the invention will be selective.

The present invention is not to be limited in scope by the specific embodiments described herein. Various modifications to these embodiments will be obvious to one of skill in the art from the description. Such modifications fall within the scope of the appended claims.

Patents, patent applications, publications, procedures and the like are cited throughout the application. These documents are incorporated by reference herein.

The invention claimed is:

1. A compound of the structure:

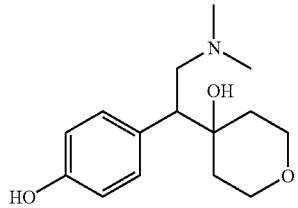

or a prodrug or a pharmaceutically acceptable salt thereof.

2. The compound according to claim 1, wherein the prodrug is an ester or ether of said compound.

3. The compound according to claim 1, wherein the prodrug is a carbamate of said compound.

4. The compound according to claim 1, wherein the pharmaceutically acceptable salt is selected from a hydrochloride, succinate or formate salt.

5. A pharmaceutical composition comprising a compound according to claim 1 and pharmaceutically acceptable carrier.

6. The pharmaceutical composition according to claim 5, comprising an oral dosage unit.

7. The pharmaceutical composition according to claim 6, wherein said oral dosage unit is a capsule or tablet.

8. The pharmaceutical composition according to claim 5, comprising an immediate release formulation.

9. The pharmaceutical composition according to claim 5, comprising a sustained release formulation.

10. A method of treating irritable bowel syndrome and urinary incontinence comprising administering a compound according to claim 1 to a subject in need thereof.

11. A method of treating depression, fibromyalgia, anxiety, panic disorder, agorophobia, anxiety, post traumatic stress disorder, premenstrual dysphoric disorder, attention deficit disorder, obsessive compulsive disorder, social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, premature ejaculation, borderline personality disorder, chronic fatigue syndrome, pain, Shy Drager syndrome, Raynaud's syndrome, Parkinson's Disease, and epilepsy, said method comprising administering a therapeutically effective amount of a compound according to claim 1.

12. The method according to claim 11, wherein the compound is formulated for once a day dosing.

13. The method of claim 11, wherein the depression is major depressive disorder (MDD).

14. The method of claim 11, wherein the method treats premature ejaculation.

* * * * *